United States Patent [19]

Nogueira et al.

[11] Patent Number: 6,113,928
[45] Date of Patent: Sep. 5, 2000

[54] SKIN COSMETIC COMPOSITION CONTAINING RETINAL

[75] Inventors: Laurent Nogueira; Nicole Peyrot, both of Toulouse, France

[73] Assignee: Pierre Fabre Dermo-Cosmetique, Boulogne, France

[21] Appl. No.: 09/117,578

[22] PCT Filed: Jan. 31, 1997

[86] PCT No.: PCT/FR97/00196

§ 371 Date: Jul. 31, 1998

§ 102(e) Date: Jul. 31, 1998

[87] PCT Pub. No.: WO97/27836

PCT Pub. Date: Aug. 7, 1997

[30] Foreign Application Priority Data

Feb. 2, 1996 [FR] France ................................. 96 01276

[51] Int. Cl.$^7$ .............................. A61K 7/00; A61K 9/107
[52] U.S. Cl. ................... 424/401; 514/725; 514/844; 514/859; 514/937; 514/938
[58] Field of Search ............................ 424/401; 514/725, 514/844, 859, 937, 938

[56] References Cited

U.S. PATENT DOCUMENTS 5,093,360  3/1992  Yu ........................................... 514/463
5,776,986  7/1998  Couval .................................... 514/698

FOREIGN PATENT DOCUMENTS

| 0391033 | 10/1990 | European Pat. Off. . |
| 4410238 | 9/1995 | Germany . |
| 9525507 | 9/1995 | WIPO . |
| 9526709 | 10/1995 | WIPO . |
| 9607396 | 3/1996 | WIPO . |

OTHER PUBLICATIONS

European Pharmacopea translation of manography for lanolin and hydrated lanolin, eight (8) pages (1997).

*Primary Examiner*—Gollamudi S. Kishore
*Attorney, Agent, or Firm*—The Firm of Gordon W. Hueschen

[57] ABSTRACT

A stable non-alcoholic cosmetic composition containing 13-trans retinal which is an oil-in-water emulsion in which the fatty phase constituents have a peroxide number no greater than about 5, and in which the fatty phase includes 10–15% by weight of capric/caprylic triglycerides and 0.02–0.5% by weight of the antioxidant BHT, and method of making the same.

5 Claims, No Drawings

SKIN COSMETIC COMPOSITION CONTAINING RETINAL

The present application is a U.S. National Application filed under 35 USC 371 of PCT/FR97/00196, filed Jan. 31, 1997 based upon French application Serial No. 96/01276 filed Feb. 2, 1996.

The present invention relates to dermocosmetic compositions containing retinal and to a process for improving their stability during storage.

Care products containing retinoids have become a center of interest in recent years. Retinoic acid, which is also known as vitamin A acid or tretinoin, is used in the treatment of acne, and there are many and varied products containing vitamin A acid.

More recently, other applications of retinoids have been revealed, such as actinic ageing. In effect, individuals who have been exposed to a great deal of sunlight during their childhood show the following characteristics in adulthood: craggy, wrinkled, yellow, saggy, rough, dry skin with hyperpigmentation, often with the appearance of various malignant growths. These phenomena are more pronounced in fair-skinned people, who burn often and do not tan.

U.S. Pat. No. 4,603,146 describes the treatment of skin damaged by exposure to the sun, using a preparation containing vitamin A acid in an emollient excipient. Subsequent to this, U.S. Pat. No. 4,877,805 disclosed that retinoids can be used to prevent and restore damage caused by sunlight on human skin.

It is also known that the use of certain retinoids, such as retinal (vitamin A aldehyde) (patents FR 94/03339 and FR 94/03970) and vitamin A esters (acetate and palmitate), are preferred to retinoic acid on account of their better skin tolerance. The reason for this is that retinal (vitamin A aldehyde), for example, occurs naturally in human metabolism: it is used in vision.

Patent FR 2,681,784 revealed the value of retinal and its precursors in the treatment of complaints such as rosacea or seborrhoeic dermatitis.

However, these are compounds with poor physicochemical stability; their formulation in a form which has good organoleptic qualities as well as good storage properties has not been satisfactorily solved to date.

For example, active retinal can be in 13-cis or 13-trans form, or in the form of mixtures thereof.

During storage, other forms tend to appear, such as 9-cis-retinal, 11-cis-retinal or condensation products of polymeric type, which are inactive.

U.S. Pat. No. 4,826,828 proposed the use of volatile silicones and ethanol for the preparation of compositions containing retinol; these preparations can be diluted before application by formation of a water/oil emulsion.

U.S. Pat. No. 4,720,353 describes water/oil emulsions stabilized with a specific organopolysiloxane.

However, these formulations do not give satisfactory storage results.

Patent application WO 93/00085 describes retinoid formulations in the form of a water/oil emulsion, stabilized with a complex system comprising a chelating agent and water-soluble and liposoluble antioxidants. EP 440,398 also relates to water/oil emulsions of retinoids.

These are formulations involving many parameters that are difficult to implement. In addition, water/oil emulsions are poorly suited to topical application, particularly in cosmetology.

Patent applications FR 94/03339 and FR 94/03970 proposed improved retinal formulations. For example, the stability of the oil/water emulsion is improved, in FR 94/03339, by using liposoluble antioxidants.

The Applicant has now found that the stability of retinal-based compositions in oil/water emulsion form can be optimized by the choice of constituents for the oily phase.

Hence, the subject of the present invention is a dermocosmetic composition containing retinal, characterized in that it is an oil-in-water emulsion and in that the constituents of the fatty phase have a peroxide number of less than or equal to about 5.

The chemical stabilization of retinal is defined by the persistent concentration of the latter in its original chemical form, this being after a defined storage duration and temperature.

The removal of any starting material having a peroxide number of greater than 5 makes it possible to obtain degrees of conservation of the retinal of greater than 97.5% after 12 months, and greater than 95.5% after 24 months, whereas it falls by 35% in standard formulations.

The peroxide number ($I_p$) is defined in the European Pharmacopeia as the number of milliequivalents of active oxygen contained in 1000 g of substance. It can be determined by methods known to those skilled in the art.

Constituents of the fatty phase that are suitable according to the invention can be chosen in particular from the group of mineral oils and waxes (paraffin, silicone, microcrystalline wax), saturated animal oils (squalane), ethoxylated, hydrogenated or natural plant oils (ethoxylated hydrogenated castor oil), fatty acid esters of polyols (glyceryl stearate) and ethoxylated derivatives thereof (glyceryl monostearate/POE) and natural or ethoxylated fatty alcohols.

The retinal can be in 13-trans, 13-cis or cis-trans form and is preferably found in the oily phase of the emulsion.

The compositions can also contain at least one antioxidant, which is preferably liposoluble. It can be chosen in particular from the group comprising: butylhydroxytoluene (BHT), butylhydroxyanisole (BHA), ascorbyl palmitate, α-tocopherol and its esters, citric acid, propyl gallate, and/or mixtures thereof; the antioxidant concentration is advantageously between 0.005% and 0.5% of the weight of the oily phase.

The retinal is preferably present at concentrations of between 0.01% and 1% of the weight of the composition.

According to one of the embodiments of the invention, the fatty phase has the following composition:

| | | |
|---|---|---|
| Liquid paraffin | 5% | |
| Squalane | 3.5% | |
| Ethoxylated hydrogenated castor oil | 1% | |
| Glyceryl monostearate/POE | 8.50% | |
| Microcrystalline wax | 1.50% | |
| Capric/caprylic triglycerides | 15% | |
| BHT | 0.02% | |
| Retinal | 0.05% | |
| 2-Phenoxyethanol | 0.50% | |
| Propyl para-hydroxybenzoate | 0.40% | |
| Butyl para-hydroxybenzoate | 0.20% | |
| Triethanolamine | 0.30% | qs pH of about 6.5 |

The subject of the invention is also a process for stabilizing a retinal-based oil/water emulsion, this process consisting in using components having a peroxide number of less than or equal to 5, with the exception of the other constituents used in the prior art, such as acetylated lanolin alcohols.

The examples which follow are intended to illustrate the invention without limiting its scope.

EXAMPLE 1
Study of the Peroxide Numbers of the Starting Materials

In a first stage, the peroxide numbers of various lipophilic or amphiphilic compounds were determined according to the method of the European Pharmacopeia, 2nd Edition, 1980, V. 3–4–5.

The lipophilic or amphiphilic compounds tested are:

| | |
|---|---|
| Neobee 18 ® | Hybrid safflower oil |
| Neobee M 5 ® | Capric and caprylic triglycerides |
| Acetulan ® | Acetylated lanolin alcohols |
| Solulan PB 10 ® | Propoxylated lanolin ether |
| Cremophor RH 40 ® | Ethoxylated hydrogenated castor oil |
| Simulsol 165 ® | Glyceryl monostearate/POE |
| Wax E ® | Microcrystalline wax |
| Cosbiol ® | Sqalane |
| Eumulgin B1 ® | Cetyl/stearyl alcohol 12-EO |

Results

TABLE 1

| Starting material | Peroxide number |
|---|---|
| Neobee 18 ® | 14.81 |
| Groundnut oil | 13.24 |
| Neobee M5 ® | 0 |
| Acetulan ® | 40.52 |
| Oat oil | 0 |
| Solulan PB 10 ® | 8.09 |
| Emulgin B1 ® | 1.67 |
| Cremophor RH 40 ® | 0 |
| Simulsol 165 ® | 0 |
| Cosbiol ® | 0.29 |
| Wax E ® | 0.50 |

The determination of the peroxide numbers reveals the sensitivity of the plant oils and of the unsaturated fatty substances and of certain amphiphilic substances toward oxygen.

EXAMPLE 2
Study of the Improvement in the Stabilization of Retinal in an Oil-in-Water Emulsion A quantitative study of the stabilization of retinal in an oil-in-water emulsion was carried out on similar formulae, which differ from each other by the absence of lipophilic or amphiphilic compounds with a peroxide number of greater than 5.

Detailed formula 1

Aqueous phase:

| | |
|---|---|
| Purified water qs | 100% |
| Carbomer | 0.25% |
| Propylene glycol | 3% |

Fatty phase:

| | |
|---|---|
| Hybrid safflower oil | 10% |
| Liquid paraffin | 5% |
| Ethoxylated hydrogenated castor oil | 1% |
| Glyceryl monostearate POE | 8.5% |
| Microcrystalline wax | 1.50% |
| Acetylated lanolin alcohols | 2% |
| Capric and caprylic triglycerides | 10% |
| Propoxylated lanolin ether | 1.50% |
| BHT | 0.02% |
| Retinal | 0.05% |
| 2-Phenoxyethanol | 0.50% |
| Propyl para-hydroxybenzoate | 0.40% |
| Triethanolamine | 0.30% qs pH of about 6.5 |
| Butyl para-hydroxybenzoate | 0.20% |

Detailed formula 2

Aqueous phase:

| | |
|---|---|
| Purified water qs | 100% |
| Carbomer | 0.25% |
| Propylene glycol | 3% |

Fatty base:

| | |
|---|---|
| Liquid paraffin | 5% |
| Squalane | 3.5% |
| Ethoxylated hydrogenated castor oil | 1% |
| Glyceryl monostearate/POE | 8.50% |
| Microcrystalline wax | 1.50% |
| Capric and caprylic triglycerides | 15% |
| BHT | 0.02% |
| Retinal | 0.05% |
| 2-Phenoxyethanol | 0.50% |
| Propyl para-hydroxybenzoate | 0.40% |
| Butyl para-hydroxybenzoate | 0.20% |
| Triethanolamine | 0.30% pH of about 6.5 |

Results

The emulsion was stored for 24 months at room temperature (in the region of 20° C.).

| Storage time at room temperature | Percentage of trans-retinal | |
|---|---|---|
| | Formula 1 | Formula 2 |
| Time 0 | 100% | 100% |
| 6 months | 95.5% | 98.5% |
| 12 months | 80% | 97.7% |
| 18 months | 76% | 96.8% |
| 24 months | 64% | 95.5% |

Formula 2 shows much better retinal stability than formula 1, with:

98.5% trans-retinal after 6 months at room temperature instead of 95.5%

96.8% after 18 months at room temperature instead of 76%, and 95.5% after 24 months at room temperature instead of 64%.

What is claimed is:

1. Stable non-alcoholic dermocosmetic composition containing 13-trans retinal, characterized in that it is an oil-in-water emulsion and in that each of the constituents of the fatty phase has a peroxide number of less than or equal to about 5, and in that it includes about 10 to about 15% by weight of the fatty phase of capric and caprylic triglycerides and about 0.02 to 0.5% by weight of the fatty phase of the antioxidant butylated hydroxy toluene.

2. Composition according to claim 1, wherein the fatty phase comprises at least one component selected from the group consisting of mineral oils and waxes; saturated animal oils; ethoxylated, hydrogenated or natural plant oils; triglycerides of fatty alcohols; fatty acid esters of polyols; ethoxylated derivatives of any of the foregoing; and natural or ethoxylated fatty alcohols.

3. Composition according to claim 1, wherein the fatty phase comprises at least one component selected from the group consisting of: paraffin, silicone, microcrystalline wax, squalane, ethoxylated hydrogenated castor oil, glyceryl stearate, and polyoxyethylated glyceryl monostearate.

4. Composition according to claim 1, wherein the fatty phase has the following composition:

| | |
|---|---|
| Liquid paraffin | 5% |
| Squalane | 3.5% |
| Ethoxylated hydrogenated castor oil | 1% |
| Glyceryl monostearate | 8.50% |
| Microcrystalline wax | 1.50% |
| Capric and caprylic triglycerides | 15% |
| Butylated hydroxytoluene | 0.02% |
| Retinal (13 trans) | 0.05% |
| 2-Phenoxyethanol | 0.50% |
| Propyl para-hydroxybenzoate | 0.40% |
| Butyl para-hydroxybenzoate | 0.20% |
| Triethanolamine | 0.30% |
| | with a pH of about 6.5 |

5. Method for the preparation of a stable non-alcoholic dermocosmetic oil-in-water emulsion containing 13-trans retinal, comprising the step of employing lipophilic constituents having a peroxide number less than or equal to about 5 as the fatty phase of the emulsion, including about 10 to about 15% by weight of the fatty phase of capric and caprylic triglycerides and about 0.02 to 0.5% by weight of the fatty phase of the antioxidant butylated hydroxytoluene, and admixing the lipophilic constituents comprising the fatty phase with the aqueous phase to constitute the emulsion.

* * * * *

UNITED STATES PATENT AND TRADEMARK OFFICE
CERTIFICATE OF CORRECTION

PATENT NO. : 6,113,928
DATED : September 5, 2000
INVENTOR(S) : Laurent Nogueira and Nicole Peyrot Tordjman It is certified that error appears in the above-identified patent and that said Letters Patent is hereby corrected as shown below:

Column 5,
Line 16, (approx): At the beginning of the line, insert, -- Polyoxyethylated --. Page 2 of Preliminary Amendment dtd 7/31/98, Claim 6, line 7

Signed and Sealed this

Second Day of October, 2001

Attest:

NICHOLAS P. GODICI
Attesting Officer    Acting Director of the United States Patent and Trademark Office